US007727734B1

(12) United States Patent
Smith

(10) Patent No.: US 7,727,734 B1
(45) Date of Patent: Jun. 1, 2010

(54) DETECTION AND MEASUREMENT OF BLOOD-FEEDING ACTIVITY

(75) Inventor: Nathan L. Smith, North Andover, MA (US)

(73) Assignee: CytoSignet, Inc., North Andover, MA (US)

( * ) Notice: Subject to any disclaimer, the term of this patent is extended or adjusted under 35 U.S.C. 154(b) by 0 days.

(21) Appl. No.: 11/494,215

(22) Filed: Jul. 27, 2006

Related U.S. Application Data

(60) Provisional application No. 60/702,914, filed on Jul. 27, 2005.

(51) Int. Cl.
*G01N 33/53* (2006.01)
(52) U.S. Cl. ..................................... 435/7.22
(58) Field of Classification Search ........................ None
See application file for complete search history.

(56) References Cited

U.S. PATENT DOCUMENTS

2004/0214172 A1   10/2004   Pfeffer et al.

FOREIGN PATENT DOCUMENTS

EP         0615128 A2    9/1994
WO         0111365 A1    2/2001

OTHER PUBLICATIONS

Morsy et al. J. Egypt. Soc. Parasitol., 24 (2) 1994: 323-331.*
Koraiem et al. J. Egypt. Soc. Parasitol., 29 (1) 1999: 131-138.*
Arbes et al. J. allergy Clin Immunol. Feb. 2003; 111(2):408-414.*
Cole et al. Contemp. Top. Lab. Anim. Sci. Sep. 2005. 44(5):27-30.*
Gamra et al 1991 Journal of the Egyptian Society of Parasitology vol. 21 No. 3 pp. 735-746.*
Morsy et al Journal of Egyptian Society of Parasitology 1994 vol. 24 No. 2 pp. 323-331.*
Robaa, S.M. in its entirety Atmosphere 2003 abstract.*
see Colloff, MJ. Progress Acarology Section 3.1.*
Arbes et al. J. Allergy Clin Immunol, vol. 111 p. 408-413, Feb. 2003.*
Mans, et al.; Evolution Of Hematophagy In Ticks: Common Origins For Blood Coagulation And Platelet Aggregation Inhibitors From Soft Ticks Of The Genus *Ornithodoros*; Mol. Biol. Evol. 19(10), 2002; pp. 1695-1705.
Quinlan, et al.; Anti-Diuresis In The Blood-Feeding Insect *Rhodnius prolixus* Stål: The Peptide $CAP_{2b}$ And Cyclic GMP Inhibit Malpighian Tubule Fluid Secretion; The Journal of Experimental Biology 200, 1997; pp. 2363-2367.

Spielman, et al.; Review: Issues In Public Health Entomology; Vector Borne and Zoonotic Diseases, vol. 1, No. 1, 2001; Mary Ann Liebert, Inc.; pp. 3-19.
Valenzuela, et al.; Purification, Cloning, And Expression Of An Apyrase From The Bed Bug *Cimex lectularius*; The Journal of Biological Chemistry, vol. 273, No. 46, Issue of Nov. 13, 1998; pp. 30583-30590.
Valenzuela, et al.; The Salivary Apyrase Of The Blood-Sucking Sand Fly *Phlebotomus papatasi* Belongs To The Novel *Cimex* Family Of Apyrases; The Journal of Experimental Biology, 204, 2001; pp. 229-237.
Valenzuela, et al.; A Salivary Nitrophorin (Nitric-Oxide-Carrying Hemoprotein) In The Bedbug *Cimex lectularius*; The Journal of Experimental Biology 198, 1995; pp. 1519-1526.
Koraiem, et al.; Studies On House Dust Mites In Great Cairo, Egypt; Journal of the Egyptian Society of Parasitology, vol. 29, No. 1, Apr. 1999; pp. 131-138.
Morsy, et al.; Isolation Of Three Species Of Mites From House Dust Of Atopic Dermatitis Patients in Qualyobia Governorate, Egypt; Journal of the Egyptian Society of Parasitology, vol. 24, No. 2, Aug. 1994; pp. 323-331.
Lane, et al.; Anti-Arthropod Saliva Antibodies Among Residents Of A Community At High Risk For Lyme Disease In California; Am. J. Trop. Med. Hyg., vol. 61(5), 1999; pp. 850-861.
Blum, et al.; A New High-Performance Reagent And Procedure For Latent Bloodstain Detection Based On Luminol Chemiluminescence; Can. Soc. Forensic Sci. J., vol. 39, No. 3 (2006); pp. 81-91.
Quickenden, et al.; The Forensic Use Of Luminol Chemiluminescence To Detect Traces Of Blood Inside Motor Vehicles; Luminescence 2004; vol. 19; pp. 271-277.
Vilkin, M.D., et al.; Performance Characteristics And Evaluation Of An Automated-Developed And Quantitative, Immunochemical, Fecal Occult Blood Screening Test; American Journal of Gastroenterology, 2005 by Am. Coll. of Gastroenterology; vol. 100; ISSN 0002-9270; pp. 2519-2525.

(Continued)

*Primary Examiner*—Robert B Mondesi
*Assistant Examiner*—Nina A Archie
(74) *Attorney, Agent, or Firm*—Hodgson Russ LLP

(57) ABSTRACT

This invention provides compositions and methods for detection of hematophagous ectoparasitic activity in an enclosure or area. The compositions comprise a reagent or reagents which are reactive against antigens or markers as they appear in the excrement or other ectoparasitic materials. Such markers or antigens may be produced by the ectoparasite itself or may have been introduced into the ectoparasite because of its blood feeding activity. The method of the present invention comprises collecting from the enclosure or area, a sample comprising environmental dust or materials and subjecting the sample to tests for detecting the presence of hematophagous ectoparasitic markers, host markers or both.

5 Claims, 4 Drawing Sheets

OTHER PUBLICATIONS

Arbes, Jr., et al.; Feasibility Of Using Subject-Collected Dust Samples in Epidemiologic And Clinical Studies Of Indoor Allergens; Environmental Health Perspectives, vol. 113, No. 6, Jun. 2005; pp. 665-669.

Cole, et al.; *Ornithonyssus bacoti* Infestation And Elimination From A Mouse Colony; Contemp. Top Lab. Anim. Sci., Sep. 2005, vol. 44(5); p. 27.

Lind et al.; The prevalence of indoor allergens in the Baltimore area: House dust-mite and animal-dander antigens measured by immunochemical techniques; Journal of Allergy and Clinical Immunology, 1987, vol. 80, No. 4; pp. 541-547; XP002489226.

Trudeau et al.; Allergenicity of the cat flea (*Ctenocephalides felis felis*; Clinical and Experimental Allergy, 1993, vol. 23, No. 5; pp. 377-383; XP002489225.

* cited by examiner

DETECTION AND MEASUREMENT OF BLOOD-FEEDING ACTIVITY

This application claims priority to U.S. Provisional application No. 60/702,914, filed on Jul. 27, 2005, the disclosure of which is incorporated herein by reference.

FIELD OF THE INVENTION

This invention relates to environmental sampling and testing in structures, shelters, or dwellings for markers associated with the presence of free-living organisms that feed on vertebrate blood.

BACKGROUND OF THE INVENTION

Hematophagy is a behavior of feeding on blood taken from vertebrate hosts. It is practiced by about 15,000 species and about 400 genera of arthropods (Mans, Louw et al. 2002). It has also been reported that blood-feeding has evolved independently at least six times. In addition to arthropods, members of other phyla including annelids such as worms and leeches are hematophagous. While independent evolution and wide-spread occurrence of taking blood-meals have resulted in considerable biological diversity, there are consistent characteristics pertinent to strategies for hematophagy including: locating and accessing a suitable blood-containing host, penetrating the integument and blood circulatory system, counteracting the hemostatic system of the host, taking a blood-meal and escaping detection so as to survive to digest the meal.

To obtain blood, hematophagous ectoparasites cut or pierce the epithelium and disrupt the integrity of the circulatory system of the host. During this process of gaining access to blood and feeding on blood, hematophages may inject substances into the host such substances being brought to the symbiotic relationship by the parasite. These injected substances may be either produced by the parasite and assist in blood-feeding or present in the hematophage as a residue of previous feeding.

Blood-feeding behavior results in numerous new infections in humans per year and many more in animals. Among the most widely known of these infections are cases of malaria resulting from mosquito bites. While Yellow fever, Chagas disease, Dengue fever, Ebola, and other diseases are transmitted by tropical insects, human arthropod-borne infections also occur in non-tropical regions. Infectious diseases such as Borrelia, Babesia, Rickettsia, West Nile virus, and various types of encephalitis infections are found in cold weather climates in the Northern Hemisphere. Similarly, many non-human species are infected by hematophagous parasites and may serve as alternate hosts or reservoirs for human pathogens.

Among blood-feeding organisms, arthropods are possibly the best known. Included in this group are arachnids (ticks and mites) and insects, flies, bugs, and lice. Some hematophagous parasites require blood-meals at every stage of life, such as is the case with ticks, lice, and bedbugs, and others only as adults and in some cases only females are parasitic. Some hematophages spend their entire life on the hosts such as is the case with head lice. Other species, such as bedbugs, get onto the source of blood only to feed. The wide biological diversity of hematophagous organisms presents a challenge to detecting and controlling these pests.

Sources of blood for these parasites are vertebrates including, most importantly, terrestrial reptiles, birds, and mammals because of their association with humans. Some species of hematophages are opportunistic and will take meals from a variety of host species whereas others may preferentially or obligately feed on one host species. In many cases humans are more exposed to hematophagous organisms upon leaving shelter. Well-known blood-sucking insects, such as mosquitoes and biting flies, and ticks, live primarily outdoors. While these parasites may enter houses, primarily to feed, they usually do not infest human shelters. Typically, arthropod life cycles are more compatible with the environment outside of human dwellings and humans are opportunistically used as sources of blood.

There are, however, animals that opportunistically share houses with humans even in developed countries. These organisms are commonly known as pests. Many arthropod pests enter a dwelling with other pests; for example, fleas may come in on rodents. It is also possible that pests enter dwellings on their own, with the humans themselves, or companion animals such as dogs or cats carry pests into the homes. Infestations by hematophagous ectoparasites can cause annoyance, discomfort, health problems, and economic losses. For example, pests in structures other than those for human habitation, including but not limited to hen houses for avian egg production, barns housing domestic animals, mammalian breeding facilities, or other structures for continued occupation by birds or mammals, may cause reduced productivity. Once inside, some arthropods are able to establish breeding colonies in the home. Often the homeowner is not aware of such infestations. For example, house dust mite colonies exist in a high percentage of homes in the United States without the human co-inhabitants being aware of their presence. These organisms feed primarily on human skin flakes that are sloughed constantly and are a component of house dust. House dust can also serve as the main nutrient source for immature fleas, obligate blood-feeders as egg producing adults.

Pesticide use to control many hematophagous species has undergone significant changes with the virtual elimination of "residual insecticides" (Spielman, Pollack et al. 2001). Subsequently, current pest management practices have not eliminated hematophagous ectoparasites from shelters: school children still are infected by head lice (*Pediculus capitas*); bedbugs (*Cimex lectularius*) infest henhouses and are being found with increasing frequency in homes and lodging facilities in the United States; fleas (*Ctenocephalides* sp.) and several genera of ticks enter structures inhabited by humans, mice, dogs, cats, and other mammals alone or in combination; and companion animals of humans are frequently hosts for are variety arachnid and insect ectoparasites. Because modern integrated pest management practices tend toward more judicious use of pesticides, determining that an infestation exists is a necessary first step in controlling pests and is useful in evaluating the effectiveness of control measures taken. Currently visual inspection either directly or using various collection and magnification aids is the primary means to determine the presence of pests. Frequent publication of articles and patents describing new and better ways to detect the presence of pests attests to the fact that current methods need improvement.

As mentioned above, blood-sucking parasites may inject substances into the host during feeding. Compounds of parasite origin have been found to have various physiological activities including anticoagulation, platelet aggregation inhibition, pain inhibition, and anti-inflammation. Such findings have lead to published studies describing the structure and function of these compounds of possible use as pharmaceuticals. Hirudin, produced by the leech *Hirudo medicinalis*, has been cloned for mass production by recombinant DNA technology and is available for treating humans as "Refludan" (BERLEX Laboratories, Wayne, N.J.). This and other therapeutic applications have lead to an expanding literature base in pharmacognosy focused on proteins, especially of salivary origin, elaborated by hematophagous invertebrates to assist in blood-feeding (Valenzuela, Walker et al. 1995; Valenzuela, Charlab et al. 1998; Valenzuela, Belkaid et al. 2001). These studies have provided DNA sequences for many salivary proteins which served as useful prior art for the present invention. Salivary biomolecules are injected into the host circulatory system where the physiological effects occur. The proteins of hematophage origin are also carried by the blood into the parasite digestive system where they become part of the blood-meal and are subject to degradation by the digestive hydrolytic processes. As a result, the structure and molecular characteristics of salivary proteins may be altered during passage through the digestive system of parasites and be different from those of the salivary proteins per se or produced from recombinant genes.

Vertebrate blood is typically about 80% water. Many hematophagous invertebrates, especially ectoparasitic species, utilize diuresis mechanisms to eliminate much of the water from a blood-meal very quickly usually as feces (Quinlan, Tublitz et al. 1997). This is necessary for many reasons including improved mobility of the pest to avoid being detected and preyed upon or swatted and more efficient digestion. The very liquid feces contain compounds that have undergone little digestion during the short time between feeding and excretion. These feces will contain biomolecular markers of blood feeding activity derived from both the host blood and those associated with the hematophagous organism involved.

Various types of tests have proven to be reliable and cost-effective for detecting biomolecules. Those skilled in the art of detecting molecules of biological origin have developed various methods to offer rapid, easy-to-use, and specific tests with sufficient sensitivity to be useful for detecting markers for a wide variety of organisms including but not limited to bacteria, viruses, parasites, and arthropods in the environment. Many of these assays take advantage of the chemical composition and of specific binding properties of biochemicals including but not limited to effectors, inhibitors, modulators, and hormones binding with receptors; lipids, metals, proteins, hormones being specifically bound to carrier proteins; antibodies binding to cell surface binding domains; and the well-know interaction between antigens and antibodies. Thus, while detection assays are know in the art, such assays have not been successfully adapted to the detection of hematophagous ectoparasites that live outside of the body of the host by the methods and compositions of this invention.

SUMMARY OF THE INVENTION

The present invention provides methods and compositions to detect infestation of an enclosure or area by hematophagous ectoparasites. This invention is based on the unexpected observation that host specific or parasite specific markers can be identified in environmental dust or other materials collected from the enclosure or area. Therefore an identification of hematophagous ectoparasitic blood feeding activity can be made in the absence of visual detection of the ectoparasites.

Accordingly, this invention provides compositions comprising a reagent or reagents to detect the presence of blood-feeding behavior and/or to provide evidence as to the identity of the hematophagous ectoparasite and/or the host. The reagents are those that react with antigens or markers as they appear in the excrement or other ectoparasitic materials (such as saliva). Such markers or antigens may be produced by the ectoparasite itself (ectoparasitic markers or antigens) or may have been introduced into the ectoparasite because of its blood feeding activity (host markers or antigens). In one embodiment, the composition comprises a regent which can react with an ectoparasitic antigen. In another embodiment, the composition further comprises a regent which is capable of detecting a host antigen (including, but not limited to, heme, hemoglobin, immunoglobulin or albumin).

The method of the present invention comprises collecting from the enclosure or area, a sample comprising environmental dust or materials and subjecting the sample to tests for detecting the presence of hematophagous ectoparasitic markers, host markers or both.

DETAILED DESCRIPTION OF THE INVENTION

Figure 1:
FIG. 1 Photograph of bedbug culture on a cardboard substrate showing dark colored spots of feces. Also shown are eggs shells as light objects.

The present invention provides methods and compositions to detect infestation of an enclosure by hematophagous ectoparasites. This invention is based on the observation that biological markers specific for the host (immediate host or a prior host) or biological markers specific to the hematophagous parasite can be identified in the excrement of the parasites. Therefore, this invention makes use of the presence, in environmental samples, of identifiable biomolecules that serve as markers of blood-feeding behavior of pests. The method comprises two steps: First, a sample representative of the environment to be tested is collected by any of many methods available including, but not limited to, vacuum collection, swabbing, scraping, shaking, or otherwise causing compounds, dust, and matter in the environment to be gathered, collected, or obtained. Such material could be collected such that it is suitable for transport. Second, the representative environmental sample is subjected to testing to detect desired biomolecule or biomolecules. From the results of the testing using commercially available reagents or the reagents of the invention, the presence or absence of hematophagous ectoparasites can be ascertained. Further, by comparing the levels of the biomolecules to a control level, the degree of infestation can also be determined.

The invention has several advantages over presently available methods of detecting ectoparasite infestations. Visual inspection is the most commonly practiced method of locating pest infestations. This is practiced by examining the environment for evidence of the pests, such as the organisms, molted exoskeletons, and/or fecal matter, by direct examination, combing, trapping, bait and trapping, or vacuuming. Hematophages have developed many different behaviors or traits to enable them to feed from the vertebrate animal without being killed, removed, or otherwise prevented obtaining blood. These behaviors or traits work against the visual methods for establishing the presence of the parasites.

Although hematophagous ectoparasites have different behaviors of blood-feeding and avoiding detection, it was unexpectedly observed that some common attributes could be used for their detection. For example, it was observed that host proteins (or partially degraded portions thereof), maintained enough integrity to be detectable in the excrement of parasites. Thus, because the pests to be detected by this invention feed on blood, based on the observations of this invention, these pests will be expected to excrete undigested and partially digested components of blood in their feces. Because the presence of vertebrate blood in the indoor environment is not normal, the presence of blood, in the absence of other known causes, can be taken as presumptive evidence of the activity of blood-feeding. In the present invention standard reagent compositions or compositions developed as provided herein, can be used detect any of a myriad of compounds derived from the host blood. For example, in one embodiment heme, present in vertebrate blood from all species, is detected to look for evidence of blood-feeding in general. In a dwelling inhabited by humans and any of a number of animal species such as dog, cats, birds, ferrets, etc., individually or in combination, detection of heme in the indoor environment indicates the possibility of blood-feeding pest infestation. Conversely, the absence of heme in house dust or other samples of the environment would provide strong evidence of the lack of hematophagous ectoparasite infestation. In another embodiment, reagent compositions could be used for detection of blood components, for example blood proteins including but not limited to hemoglobin, albumin, or immunoglobulins, with more specificity than detecting heme which is present in hemoglobins of all vertebrates.

A second common trait that enables and accompanies blood-feeding is injection of salivary compounds of parasite origin into the wound in the host. These compounds, mostly proteins as discussed above, appear in the gut of the blood-sucking pest. As a result of the diversity of hematophages, these compounds vary highly in structure and composition even if not in function. The invention teaches that specificity will be increased by taking advantage of this biochemical diversity.

The method and selected reagents of this invention could be used to detect hematophagous ectoparasites including bedbugs and other bugs, lice, mites, fleas, mosquitos, flies, and ticks Those species of particular interest are those that can infest dwellings used by their hosts. In one embodiment, bedbugs (*Cimex lectularius*) and *Pediculus humanus* (human head and body louse) are detected by the method of this invention.

Broadly, it is an object of the instant invention to provide compositions of prescribed reagents to detect the presence of blood-feeding behavior and to also provide evidence as to the identity of the ectoparasitic hematophages involved. The reagents will be those that react with antigens or markers as they appear in the excrement or other ectoparasitic materials (such as saliva). Such markers or antigens may be originating from the ectoparasite itself (ectoparasitic markers or antigens) or may have been introduced into the ectoparasite because of its blood feeding activity (host markers or antigens). Non-limiting examples of such markers or antigens are those that are present in the excrement and/or saliva of the ectoparasite—whether due to being produced by the ectoparasite or derived from a host on whom the ectoparasite has previously fed. In one embodiment, the composition comprises a regent which can react with an ectoparasitic antigens. In another embodiment, the composition further comprises a regent which is capable of detecting a host antigen.

In the present invention, testing may be performed on an environmental sample depending on the information that is to be obtained. For example, testing may be directed to detecting all blood feeding activity (such as detection of heme in the environmental sample), detecting blood feeding on humans (such as by using probes specific for human blood proteins, detecting for the presence of all blood feeding pests (such as by detecting salivary proteins of pest-origin), or the presence of specific blood feeding pests (such as by detecting species specific salivary proteins). Those skilled in the art will recognize that any combination or routine modification of the above can be used depending upon the information desired.

The method of the present invention can be useful in detecting blood-feeding activity in such places as: multi-room homes; hotels, motels, hostels, dormitories, boarding houses, shelters, and any other facilities in which people live or otherwise occupy; transportation related enclosures such as cruise ships, railway sleeping cars, airplanes; and animal housing enclosures such as henhouses, indoor rodent colonies, vivaria, and non-carnivorous animal breeding establishments. In multi-room establishments, samples, such as dust captured by vacuuming, can be collected from each room and tested for the presence of, for example, hemoglobin. Those rooms that test positive can be subjected to treatment or additional testing.

In one embodiment, the invention can also be used to discriminate between blood feeding organisms of different species or blood feeding organisms feeding on more than one species. Therefore, the method of the present invention could be used in structures where more that one vertebrate species may be present either intentionally or by happenstance. In these cases the composition of the testing reagent can be selected to be specific for detecting hemoglobin, or other blood substance, of the species of interest. For example, a number or reagents are available (or can be produced by standard techniques) which react specifically with human and which do not react with hemoglobins from cats, dogs, or rodents. Such reagents can be used to specifically test for blood feeding parasite activity on humans. Alternatively, a reagent specific for canine hemoglobin could be used to differentiate between parasites feeding on dog blood from those feeding or humans, cats, and rodents. Such compositions can be useful in homes occupied by people and their vertebrate pets and in barns occupied by a colony of domestic animals and also possibly by vertebrate pests. In such a test, the presence of blood-feeding activity and the host could be determined by using reagents similar to those currently used to obtain species identity of blood stains in forensic serology. For example, recently, a human hemoglobin specific rapid field-use forensic test has been introduced by BlueStar, ROC Import, Monte Carlo, Monaco. This test gives positive results for human hemoglobin while being negative for blood from non-primate animals. The same art has been utilized by several of the immunological FOBT described herein to allow for detecting human hemoglobin without giving false positive reactions with non-human hemoglobin.

A second embodiment of the present invention is to test for the presence of a marker of parasite origin in samples. This method is preferred in situations in which detecting compounds derived from host blood might not be sufficient to confirm the infestation. This method would also be useful in determining the identity of the pest. It is important in selecting the composition of the reagents to practice this embodiment to identify the structure and binding properties of the biomolecule or biomolecules to be detected as they exist in the environment dust samples. These properties may or may not differ from those of the native molecule as produced in the digestive system, including salivary glands. Therefore, in spite of knowing the gene sequence and protein structure, the properties of the biochemicals of interest may be altered by passage through the digestive system and release into the environment. This art has been practiced to increase specificity of immunoassays including the FOBT produced by Care Products, Waterbury, Conn. In this test, antibodies selected for use are specific to hemoglobin released into the distal gut and not to the more extensively degraded hemoglobin emanating from mouth, stomach, and proximal gut locations.

A third embodiment is detecting in the environment dust samples comprising excrement of hematophagous ectoparasites, one or more markers indicative of a previous feeding of the pest. For example, a tick becomes infected with Borrelia, the Lyme Disease organism, by feeding on a small rodent infected with the organism. During a subsequent feeding on humans, the infected tick may inject Borrelia microorganisms into the bloodstream of that host with saliva. Some of the Borrelia organisms thus injected can then be ingested by the ectoparasite that injected them. Therefore, the excrement of the ecotoparasite may contain not only the markers for the immediate past host (in this example a human), but also a marker obtained by the ectoparasite from a prior host (in this example Borrelia). In manner similar to that described for blood components and salivary compounds, compounds of microbial origin may be found in excreted materials. Microbes, molecules, or markers derived therefrom are then available for detection in environmental samples. Such tests could be very valuable for epidemiological studies where catching organisms is not practical.

In the method of the present invention, collection of an environmental sample is the first step in detecting presence of hematophages. The terms "environmental dust sample" or "environmental dust" as used herein refers to materials collected from an enclosure that can be expected to contain the excrement, which in turn contains markers of blood feeding by pests. Such environmental dust sample or environmental dust may comprise materials including flakes and smears from diuresis elimination of water by pests described previously; shells, casts, casings, and any other remnants of the blood-feeding pest bodies or eggs; and fecal matter containing markers as described herein. Any method by which an environmental sample or environmental dust can be collected, can be used. One well-established method is the vacuum trace evidence collection practiced in crime scene investigations. These systems are commercially available (a vacuum evidence collection kit is offered by, for example, 3M, Minneapolis, Minn.) The utility of these systems has been well accepted in criminal investigative work. Disposable filters and sealable plastic containers, designed to maintain sample integrity and chain of custody, might be well suited to collect samples in the instant invention. In addition, other sample collection methods to be used include collecting dust accumulated on home HVAC filters; filters in room air conditioners in hotels and motels; dust accumulated on or near ventilation fans in barns, stables, henhouses, etc.; dust collected by electrostatic particle precipitators; and samples collected by damp mopping non-porous floors such as tile floors in schoolrooms. Specific sample collection methods are not necessary to practice the invention but the validity and therefore the utility of the results are dependent upon collecting and maintaining the integrity of a representative Sample. For example, in a room with a suspected blood-feeding pest infestation, it might be deemed useful to vacuum the whole room to screen for markers; to manually collect dark-colored flakes around the head of the bed; to vacuum only around the head of the bed to look more specifically for bedbugs due to their feeding habits; to lift materials with water-dampened swabs; or possibly all or any combination of collection methods. All samples thus obtained could be tested for any or all markers depending upon judgment of the persons involved, costs, desired thoroughness, etc. All or a portion of the collected materials in the environmental dust sample is then used for detection of blood feeding activity.

The second step in the invention is to test for marker or markers indicative of blood feeding activity. The invention provides for selecting reagents depending upon the specific inquiry. For example, reagents can be used for detection of heme, which is present in all vertebrate blood and is expected to be present in the excrement of all blood-feeding parasites following blood feeding activity. The invention also provides for species specific screening for a marker or markers such as using monoclonal or polyclonal antibody based immunoassays to differentiate human hosts from animal hosts, for example. Examples of such reagents include antibodies (including antigen binding fragments thereof) to species specific blood proteins as described herein for human hemoglobin and IgG. The invention also provides for parasite specific screening, that is, testing for markers that differentiate a parasite species from others without providing information on the host species. The invention further provides for combinations of reagents or test components designed to provide relevant information for the conditions encountered. Further, the method provides for detecting marker or markers released into the environment by blood-feeding said marker or markers being present in the pest as a result of previous feeding or feedings.

Detecting components of the blood of the host or those derived from the parasitic organism may be accomplished by direct chemical methods such as guaiac oxidation, cyanmethemoglobin tests or more specific ligand-binding assay, such as immunoassay, nucleic acid based detection methods or other suitable methods.

Examples 1, 2 and 3, provide details on the methods to detect vertebrate hemoglobin in hematophagous insect feces using chemical reactions involving the metalloporphyrin moiety present in hemoglobin from all vertebrate species. One method is based on reaction between heme of hemoglobin with guaiac after which a developer solution containing hydrogen peroxide is added. If hemoglobin is present, the guaiac is oxidized, turning the detection reagent blue. In addition, several other methods that might be used to detect hemoglobin in samples collected could be used. One of particular interest, because of its well-established sensitivity would be luminol spray used successfully by forensic scientists to visualize bloodstains not visible to the human eye. Samples can be collected by vacuum onto a barrier filter membrane as described herein and as practiced in forensics. The membrane can be removed and placed into a dark chamber in view of a sensitive camera. Either film or digital photography could be employed. A luminol solution (such as from BlueStar), can be sprayed onto the membrane and sample material associated thereto and chemiluminescence, if any, would be recorded by the camera suitably setup and activated.

Liquid Samples, such as those obtained by mopping an enclosure, or a water extract of a dust sample can also be used. The use of the cyanomethemoglobin method (with Drabkin's reagent described in Drabkin, D. L., Austin, J. H. *Journal Biological Chemistry* 112, 51, (1935)) to detect and measure hemoglobin is well established in diagnostic and veterinary medicine and can be used in this embodiment by adding the sample to the reagent and test for the development of the specified color.

In Examples 4 and 5, immunological determination of human hemoglobin in hematophagous arthropod feces is disclosed. These examples demonstrate that proteins, as exemplified by the globin portion of hemoglobin, present in the blood-meal retain antigenic characteristics that enable testing for the protein using immunochemical reactions. In addition to the immunological fecal occult blood test (iFOBT) other antigens including animal blood proteins and salivary proteins of parasite origin, and antigens associated with infectious disease causative agents such as malaria, West Nile virus, trypanosomiasis, etc, can also be used. To accomplish this, commercially available antibodies (such as directed against canine hemoglobin or chicken hemoglobin) can be used or antibodies specific for markers of interest may produced using hematophages or parts or products of hematophages such as feces. Commercially available antibodies, raised against intact proteins isolated from host blood, can also be used as reagents of the invention. Alternatively, or additionally, antibodies can also be generated against proteins present in the feces. This will address the issue of degradation of antigenic epitopes during the digestive process. A similar approach can be used for salivary proteins produced by the hematophagous arthropod. Once antibodies are obtained either commercially or raised against the proteins or peptides, the antibody can then be validated for use by establishing reactivity with antigens in feces. Such antibodies can be employed in any of various immunoassay techniques available to those skilled in the art including but not limited to immunochromatographic or lateral flow techniques, ELISA, double diffusion, particle agglutination, immunoprecipitation, laser and non-coherent light nephalometry, and immunoinhibitory assays. The selection of the technique will be made based on the requirements of the Sample, the information being sought, and the venue in which the test will be performed.

Examples 6 and 7 describe results obtained with environmental samples collected from a multiplicity of rooms in hotel building operating commercially. In addition to testing for hemoglobin using methods of preceding Examples, the versatility, adaptability, and broad applicability of the present invention is disclosed by successfully testing for IgG, a blood protein, in the environmental samples (Examples 8). Examples 9 describes a combination of immunological and chemical detection methods. Example 10 describes results obtained from a sample collected from non-human housing structure.

Examples 11-13 demonstrates the feasibility of generation of antibodies to salivary antigens of hematophagous ectoparasites such that the antibodies can be used for detection of the parasites in parasitic excrements or environmental dust samples from enclosures.

The following Examples describe the preliminary results obtained in experiments conducted prior to filing this application.

EXAMPLE 1

Detecting Heme-Iron in Bedbug Culture Substrate

Cultures of bedbugs (*Cimex lectularius*) were maintained in glass jars containing a pressed paper cardboard substrate (FIG. 1) at room temperature and were allowed to feed at 7 to 14-day intervals on human blood. The bedbugs were allowed access to human skin through a 200-mesh nylon screen attached over the top of their jars. The skin was allowed to be in contact with the mesh for at least 10 minutes with each jar during which time the bedbugs fed to repletion. Cardboard substrate was removed from each jar at least 10 days after feeding, put into plastic bags, sealed, and stored in the freezer at temperatures below $-10°$ C. until processed.

Figure 2:
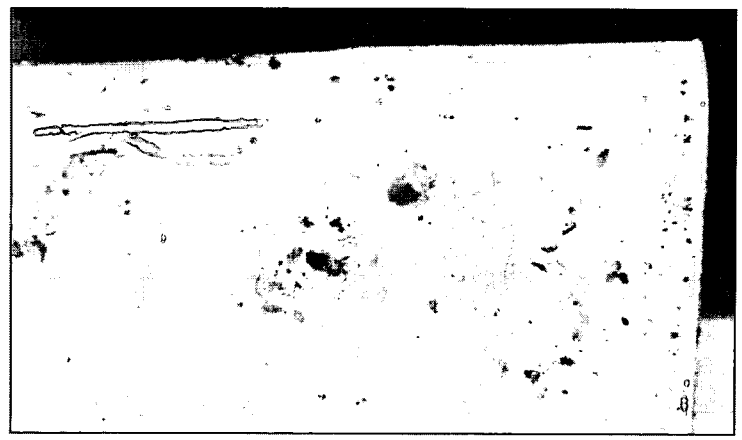
FIG. 2 Photograph of bedbug culture debris containing exoskeleton molts (large objects) and small, dark colored fecal matter.
Figure 3:
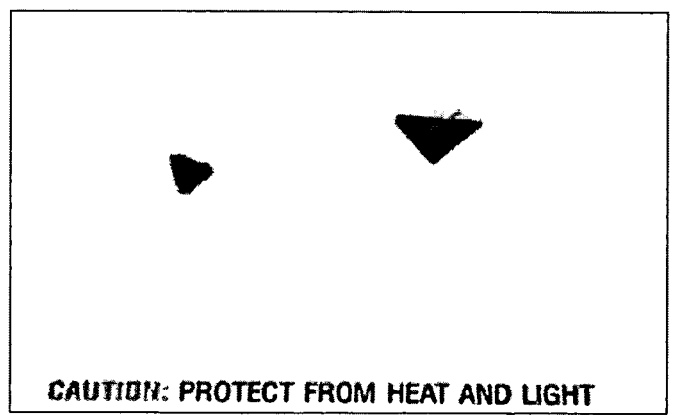
FIG. 3 Photograph of samples cut from bedbug culture substrate cardboard shown after being used in guaiac fetal occult blood test (FOBT).

Fecal occult blood tests (FOBT) of two different peroxidase activity visualization chemistries were used from three different commercial suppliers (guaiac from Immunostics, Inc., Ocean, N.J. and Care Products, Waterbury, Conn. and 3,3',5,5'-tetramethyl benzidine (TMB) from Biomerica, Inc., Newport Beach, Calif.) were used to qualitatively detect heme. Samples tested were bedbug culture debris (an example of which is shown in FIG. 2) and pieces of the cardboard cut from the substrate (such as shown in FIG. 3).

Figure 4:
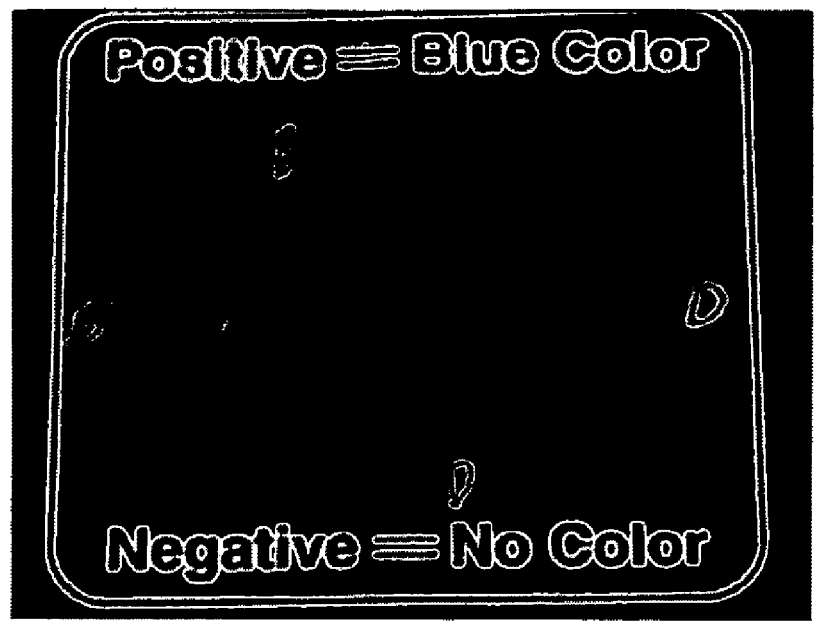
FIG. 4 FOBT (Biomerica) results with bedbug culture extract ("B") and office dust extract ("D"). Note positive reaction with B and no color development with D.
Figure 5:
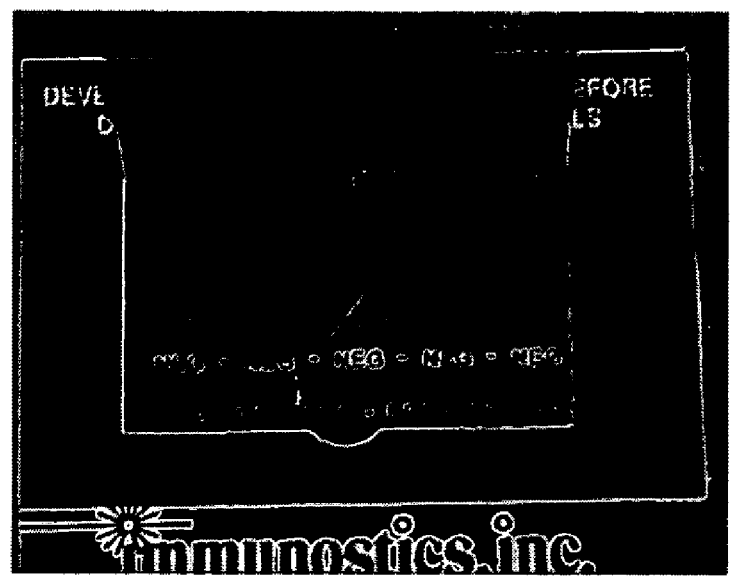
FIG. 5 Photograph of FOBT (Immunostics) showing office dust extract on left and bedbug culture extract on right. A positive reaction is seen with only with the bedbug extract.

Extracts were made by putting bedbug culture debris into vials of buffer supplied by Care Products for the immunologic FOBT and shaken for about 5 minutes. Two drops of these extracts were placed on EZ Detect pads (Biomerica, Inc.) employing the TMB chemistry and processed according to manufacturers instructions. FIG. 4 shows the results with clear development of color (positive result) with the bedbug culture extract. FIG. 5 shows the results of the same extracts run with Immunostics' guaiac FOBT. In addition, pieces of the culture substrate, such as shown in FIG. 3, were placed on the paper of both the Immunostics and Care Products guaiac FOBT. Upon addition of the developing reagent, positive results were observed. A molted exoskeleton gave a negative result in guaiac FOBT.

It can be concluded from these results that the peroxidase activity such as that of hemecan be detected in the feces of bedbugs

EXAMPLE 2

Detection of Blood in Bedbug Cultures Using Luminol

Figure 9:
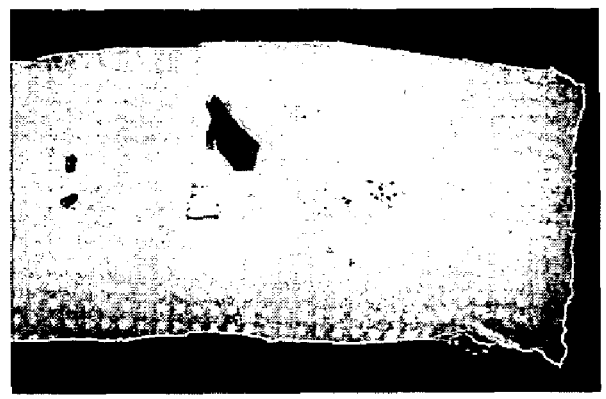
FIG. 9 Photograph showing bedbug culture debris placed on plastic backed absorbent paper. Two (2) exoskeleton molts can be seen on left. Feces and other debris are shown on right side of paper.
Figure 10:
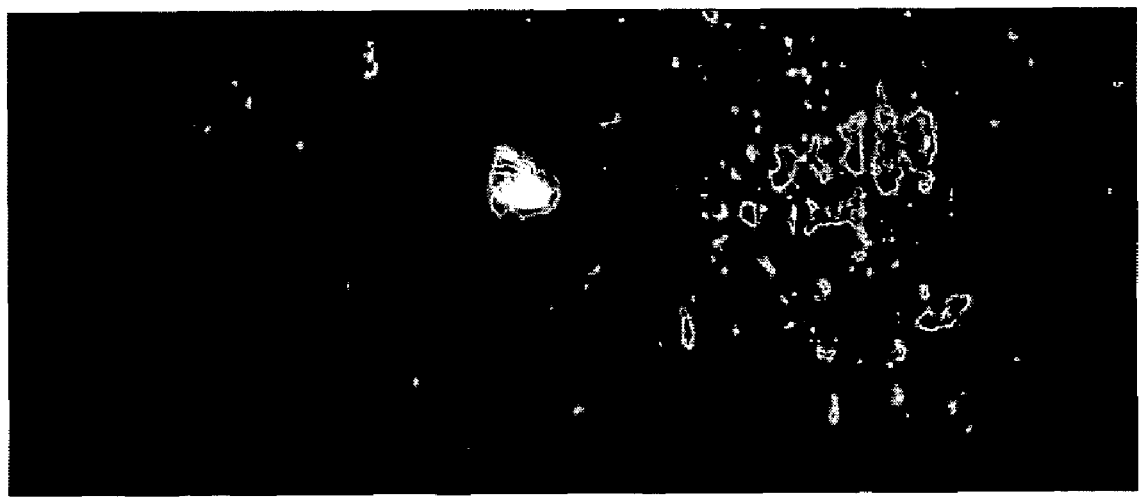
FIG. 10 Bedbug culture debris preparation shown in FIG. 9 after treatment with luminol (BlueStar).

Debris collected from bedbug cultures as in Example I was placed on absorbent plastic-backed paper (FIG. 9) and sprayed with a commercially available luminol blood visualization solution (BlueStar, ROC Import, Monte Carlo, Monaco). The resultant chemiluminescence was seen to be associated with the debris and not with the molted exoskeletons (FIG. 10). This visualization technique can be used as in initial step to identify individual or clusters of particles emitting light to be isolated and subjected to further testing to confirm hematophage activity.

EXAMPLE 3

Detection of Blood in Bedbug Cultures Using Urine Test Strips

Debris collected from bedbug cultures as in Example I was dissolved in water and tested for the presence of blood using commercially available urine dipsticks (such as from Roche or Bayer). With each test the presence of detectable blood was indicated by positive reaction on the appropriate pads.

EXAMPLE 4

Detection of Human Hemoglobin in Bedbug Cultures with Monoclonal Antibodies

Figure 6:
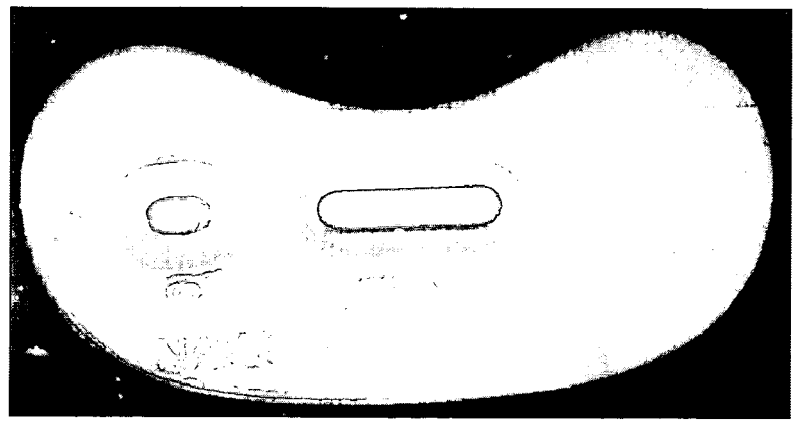
FIG. 6 Photograph of single-use cartridge (IMMOCARE) showing the sample addition site (labeled "S") and the zones labeled "C" where the control line develops in a valid test. If a line develops in the area labeled "T", the test is positive and human hemoglobin has been detected. No line is a negative result. In addition to the cartridge, a vial of buffer is supplied to prepare a suspension and extract of the sample.
Figure 7:
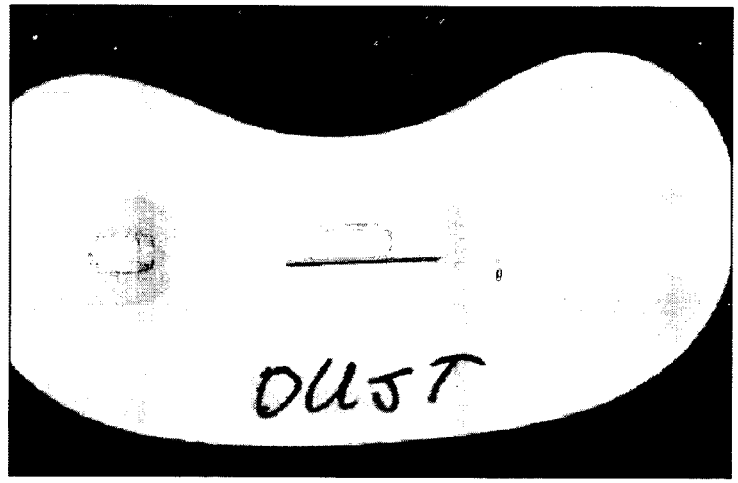
FIG. 7 Photograph of office dust extract run on a cartridge similar to one shown in FIG. 6. Negative result indicates no human hemoglobin was detected.
Figure 8:
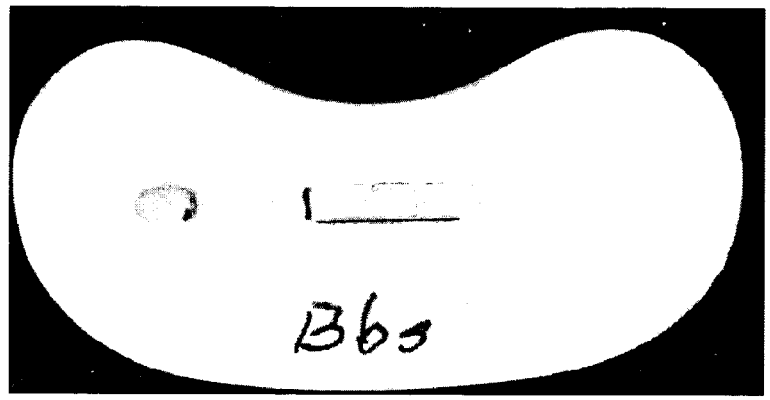
FIG. 8 Photograph shows result of ImmoCARE IMMOCARE FOBT with bedbug culture debris extract. Strong line at "T" shows a positive result indicating presence of human hemoglobin.

The culture debris extracts from Example I were also tested with IMMOCARE (immunological FOB from Care Products, Inc. Waterbury, Conn.). The suspensions were added to cartridges (FIG. 6) provided with the kit and allowed to develop according to the instructions. The results were read per the instructions and are shown in FIGS. 7 and 8. The bedbug culture debris extract clearly gave a positive result indicating that sufficient epitopes were present of the hemoglobin in the feces to react with the monoclonal antibodies in the iFOBT.

EXAMPLE 5

Detection of Human Hemoglobin in Bedbug Cultures with Polyclonal Antibodies

The culture debris extracts from Example I were tested for reactivity with commercially available polyclonal raised against human hemoglobin by direct and sandwich immunoassays. For direct detection, 20 µL of extract was applied to nitrocellulose membranes and washed to remove unbound materials. The membranes were blocked with 20% horse serum in buffered saline and washed 3 times. Spotted membranes were incubated with 2% horse serum-saline alone or containing polyclonal anti-hemoglobin labeled with horseradish peroxidase (HRP) or alkaline phosphatase (AP) and washed to remove unbound enzyme-labeled antibody. Any enzyme activity bound via antibody to antigen present in the debris extract bound to the membrane was visualized with the appropriate substrate. Clearly visible colored spots were observed when spotted membranes were exposed to enzyme labeled anti-hemoglobin and the appropriate substrate while no visible reaction was observed when either substrate was exposed to spotted membranes not allowed to react with antibody.

Sandwich immunoassays for hemoglobin in culture debris by immobilizing polyclonal anti-hemoglobin to nitrocellulose membranes, washing, and blocking as described above. The capture antibody membranes were then allowed to incubate with culture debris extract, washed, and exposed to enzyme labeled anti-hemoglobin. After visualization with enzyme substrate, the presence of hemoglobin in the culture debris was indicated by developed color.

Bedbug culture debris was incubated with affinity purified polyclonal anti-hemoglobin to occupy epitopes necessary for positives reaction in iFOBT assays of Example 4 or immunoassays of Example 5. In all cases, prior treatment of the antigen with anti-hemoglobin prevented detection of hemoglobin by the immunoassays described in the cited Examples.

EXAMPLE 6

Detection of Hemoglobin in Environmental Samples—Sample Collection

Examples 1 through 5 demonstrated that evidence of blood feeding by hematophagous organism can be obtained from the organisms' fecal debris. To establish the utility of these methods for detecting naturally occurring blood feeding by testing environmental samples, samples were collected from offices, hotel rooms, and homes. Samples were collected by methods described herein including using standard vacuum cleaners to collect vacuum bag dust, using handheld portable vacuum devices, manually removing dust collected on filters of HVAC systems, air conditioners, and fans, and collecting dust manually or by wiping. Dust samples thus collected were used directly without further treatment or extracted with any of a variety of aqueous solutions to prepare liquid samples in the examples that follow.

EXAMPLE 7

Samples from Office and Hotel Rooms—Testing for Environmental Hemoglobin as Evidence of Blood Feeding Vacuum dust collected by vacuuming and manually removed from air conditioner filters from individual rooms were tested with luminol by spraying the test solution onto dust samples as collected. Some vacuum dust samples gave positive chemiluminescence with various densities of light emitting particles per volume of dust while other samples gave no visible chemiluminescence. Samples of dust from filters of air conditioners, such dust being a capture or aerosolized particles over time, were uniformly negative for chemiluminescence when tested with luminol. These results indicate that the luminol test has sufficient sensitivity to be useful in the present invention.

The samples were also tested for hemoglobin using FOBT and test strips giving results consistent with the luminol results. These results also indicate that testing for the heme moiety is useful for screening, that is to eliminate sites without detectable blood-feeding activity and therefore possible infestation from further investigation at a given time.

EXAMPLE 8

Samples from Hotel Rooms—Testing for Human IgG as Evidence of Blood Feeding

Samples from bedbug cultures and environmental samples were extracted with dilute (0.001 N) sodium hydroxide, neutralized by addition of 0.2 M potassium phosphate in 0.9% NaCl, and tested at various dilutions for the presence of human IgG, a blood serum protein, using a commercially available enzyme linked immunosorbent assay (ELISA) test kit (ZeptoMetrix Inc., Buffalo. NY). Positive results for IgG in environmental samples as well as Cimex culture debris indicated the potential utility of testing for blood components other that hemoglobin for screening or detecting blood feeding activity. These results demonstrate that that proteins other than the globin moiety of hemoglobin remain sufficiently structurally intact after the digestive process by Cimex to be detectable by standard immunological reagents and means.

The result also provide support for the idea that the methods and compositions of the present invention can be designed to be applicable to a variety of testing requirements.

EXAMPLE 9

Detecting Hemoglobin by Combined Immunological and Chemical Methods

Culture debris and environmental samples from previous examples were further tested with an immunoassay and luminol combination method. Test membranes to which monoclonal antibodies specific for human antibodies were removed from the iFOBT devices previously described. In addition, approximately 1 microgram of polyclonal anti-human-antibody obtained commercially from Bethyl Labs, Montgomery, Tex., was immobilized on a nitrocellulose membrane strip. Both sets of antibody test strips were washed in PBS and coated with 10% normal horse serum in PBS for 30 min. Hotel room and culture debris extracts, also in PBS, were added to the strips for 2 hours at room temperature. Test strips not exposed to the extracts were included in the experiment as negative controls. After incubation with the samples or control, all strips were washed 3 time with PBS. Each strip was sprayed with luminol solution as previously described and examined for chemiluminescence which was clearly observed with the antibody strips exposed to samples. In the control strips no chemiluminescence was observed at the location of the immobilized antibody. This experiment demonstrates that analytical methods can be used alone or combined to depending upon the testing needs.

EXAMPLE 10

Samples Chicken Houses—Environmental Samples

Samples of dust from the floor, trays, fans, and fan filters were collected from structures housing chickens. Some of the birds were in individual cages and some were in groups of several dozens free to move about contained in open rooms. Positive chemiluminescence and dip stick tests were obtained with samples but all tests using immunoassays specific for human hemoglobin were negative. These results demonstrate the capability to design test reagents and systems for detecting ectoparasitic blood-feeding on animal hosts and the ability to differentiate such activity from that occurring with human hosts.

EXAMPLE 11

Antibodies Against Hematophage Antigens

Blood was drawn by a healthcare professional from a human volunteer who had been bitten by Cimex repeatedly for more than 3 years and who had consented to provide blood and have it tested for reactivity with samples obtained as described herein. Plasma was prepared, separated and frozen. To determine the presence of antibodies against antigens present in bedbug culture debris, a debris extract was applied to nitrocellulose membranes as in Example 5, washed, blocked with 2% normal horse serum in PBS, and exposed to human plasma from above at various dilutions. The membranes were then washed and allowed to incubate with alkaline phosphatase labeled anti-IgG (human). The presence of antibodies to antigens present in the bedbug culture debris was visualized by exposing the membrane so treated with substrate for alkaline phosphatase. The presence of color was observed at antiserum concentrations higher than at a 1:500 dilution and was not observed on membranes not exposed to the human antibody solutions. These results indicate that antibodies produced in response to exposure to hematophage saliva can be used for detecting the presence of pest excrement. Such presence could indicate past or present blood feeding activity.

EXAMPLE 12

Collection of Cimex Saliva

Saliva was collected from bedbugs immobilized with adhesive tape by positioning the mouthparts of the insect into a capillary tube. A solution of pilocarpine in alcohol sufficient to induce saliva excretion in the individual being used was applied to the head of the insect. The saliva thereby secreted was collected in the capillary, transferred to vials, sealed, and frozen until used.

EXAMPLE 13

Testing of Reactivity of Antibodies Against Hematophage Salivary Antigens

Human antibodies preparation collected as described in Example 11 was tested with Cimex saliva described in Example 12 by immobilizing proteins on to nitrocellulose membranes, blocking and washing as previously described. The membranes were incubated with human antibodies at dilutions varying from 1:50 to 1:1000 in PBS containing 2% normal horse serum and the reactivity was detected with enzyme-labeled-anti-human IgG as previously described. Color development indicated reaction between the saliva sample and human antibodies. The reactivity was similar to that observed in Example XI and was consistent with the presence of immunologically detectable hematophage specific markers in saliva. This example demonstrates that antibodies generated from individuals who have been bitten by the hematophagous parasites (and therefore exposed to the salivary proteins of the parasites) can be used for the detection of parasites in an environmental sample. Thus polyclonal or monoclonal antibodies from individuals (humans or animals) could be obtained following exposure to the parasitic antigens such as salivary proteins—whether by being bitten by the parasite or other conventional immunization procedures. Because the volunteer donor reported redness and itching as a result of bedbug bites—a physiological reaction associated with an immunoreaction to substances injected in saliva—these results support the conclusion of the inventor that the invention will have utility in testing for any blood-feeding ectoparasite to which the host mounts an immune response.

REFERENCES

1. Mans, B. J., A. I. Louw, et al. (2002). "Evolution of hematophagy in ticks: common origins for blood coagulation and platelet aggregation inhibitors from soft ticks of the genus *Ornithodoros*." *Mol Biol Evol* 19(10): 1695-705.
2. Quinlan, M., N. Tublitz, et al. (1997). "Anti-diuresis in the blood-feeding insect *Rhodnius prolixus* Stal: the peptide CAP2b and cyclic GMP inhibit Malpighian tubule fluid secretion." *J Exp Biol* 200(17): 2363-2367.
3. Spielman, A., R. J. Pollack, et al. (2001). "Issues in Public Health Entomology." *Vector-Borne and Zoonotic Diseases* 1(1): 3-19.

4. Valenzuela, J. G., Y. Belkaid, et al. (2001). "The salivary apyrase of the blood-sucking sand fly *Phlebotomus papatasi* belongs to the novel Cimex family of apyrases." *J Exp Biol* 204(Pt 2): 229-37.
5. Valenzuela, J. G., R. Charlab, et al. (1998). "Purification, cloning, and expression of an apyrase from the bed bug *Cimex lectularius*. A new type of nucleotide-binding enzyme." *J Biol Chem* 273(46): 30583-90.
6. Valenzuela, J. G., F. A. Walker, et al. (1995). "A salivary nitrophorin (nitric-oxide-carrying hemoprotein) in the bedbug *Cimex lectularius*." *J Exp Biol* 198(Pt 7): 1519-26.

The invention claimed is:

1. A method of determining a likelihood of blood feeding activity by a hematophagous ectoparasite in an enclosure inhabited by individuals of a host species, wherein the hematophagous ectoparasite is a bedbug, the method comprising the steps of:
   a) collecting a sample of environmental dust from the enclosure;
   b) detecting for the presence or absence in the environmental dust sample of a marker selected from the group of markers consisting of host hemoglobin, hematophagous ectoparasite salivary protein antigens, and combinations of host hemoglobin and hematophagous ectoparasite salivary protein antigens, which host hemoglobin marker or hematophagous salivary protein antigen marker is detectable in excrement of the hematophagous ectoparasite,
   wherein detecting the presence of the marker in the environmental dust sample is indicative of a likelihood of blood feeding activity by the hematophagous ectoparasites feeding on the inhabitants of the host species in the enclosure and wherein the absence of the marker in the environmental dust sample is indicative of a likelihood of a lack of blood feeding activity by the hematophagous ectoparasites feeding on the inhabitants of the host species in the enclosure.

2. The method of claim 1, wherein the environmental sample is collected by vacuuming, swiping or mopping.

3. The method of claim 1, wherein the host species is selected from the group consisting of human, dogs, cats, rodents and chickens.

4. The method of claim 1, wherein the enclosure is inhabited by humans.

5. The method of claim 1, wherein the enclosure is inhabited by non-human animals or birds.

* * * * *